United States Patent
Ishihara

(10) Patent No.: US 11,822,270 B2
(45) Date of Patent: Nov. 21, 2023

(54) IMAGE FORMING APPARATUS, PRINTING CONTROL METHOD, AND CONTROL PROGRAM

(71) Applicant: KONICA MINOLTA, INC., Tokyo (JP)

(72) Inventor: Keita Ishihara, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/871,695

(22) Filed: Jul. 22, 2022

(65) Prior Publication Data
US 2023/0068429 A1 Mar. 2, 2023

(30) Foreign Application Priority Data
Aug. 25, 2021 (JP) .................................. 2021-136853

(51) Int. Cl.
G03G 15/20 (2006.01)
G03G 15/00 (2006.01)
A61L 2/00 (2006.01)

(52) U.S. Cl.
CPC .......... G03G 15/205 (2013.01); A61L 2/0023 (2013.01); G03G 15/5016 (2013.01); A61L 2202/14 (2013.01); G03G 2215/00772 (2013.01)

(58) Field of Classification Search
CPC ........ A61L 2/0023; G03G 2215/00772; G03G 15/5016; G03G 15/205
See application file for complete search history.

(56) References Cited

U.S. PATENT DOCUMENTS 10,295,952 B2 * 5/2019 Hashimura .......... G03G 21/105

FOREIGN PATENT DOCUMENTS

JP 2016018025 A 2/2016

* cited by examiner

Primary Examiner — Victor Verbitsky
(74) Attorney, Agent, or Firm — Holtz, Holtz & Volek PC

(57) ABSTRACT

An image forming apparatus includes: sheet feeding trays; an image forming part that includes a fixing part and forms an image on a sheet fed from each of the sheet feeding trays based on a print job; and an acquisition part that acquires information indicating "presence" or "absence" of a possible carrier having a possibility of virus infection in a region where an apparatus main body is installed; and a hardware processor that is able to select an operation mode of the print job from a normal mode and a virus removal mode, and sets an operation mode of the print job to the virus removal mode, wherein in the virus removal mode, a fixing temperature of the fixing part is set to a predetermined temperature, and a heating time for the sheet in the fixing part is made longer than a heating time in the normal mode.

21 Claims, 16 Drawing Sheets

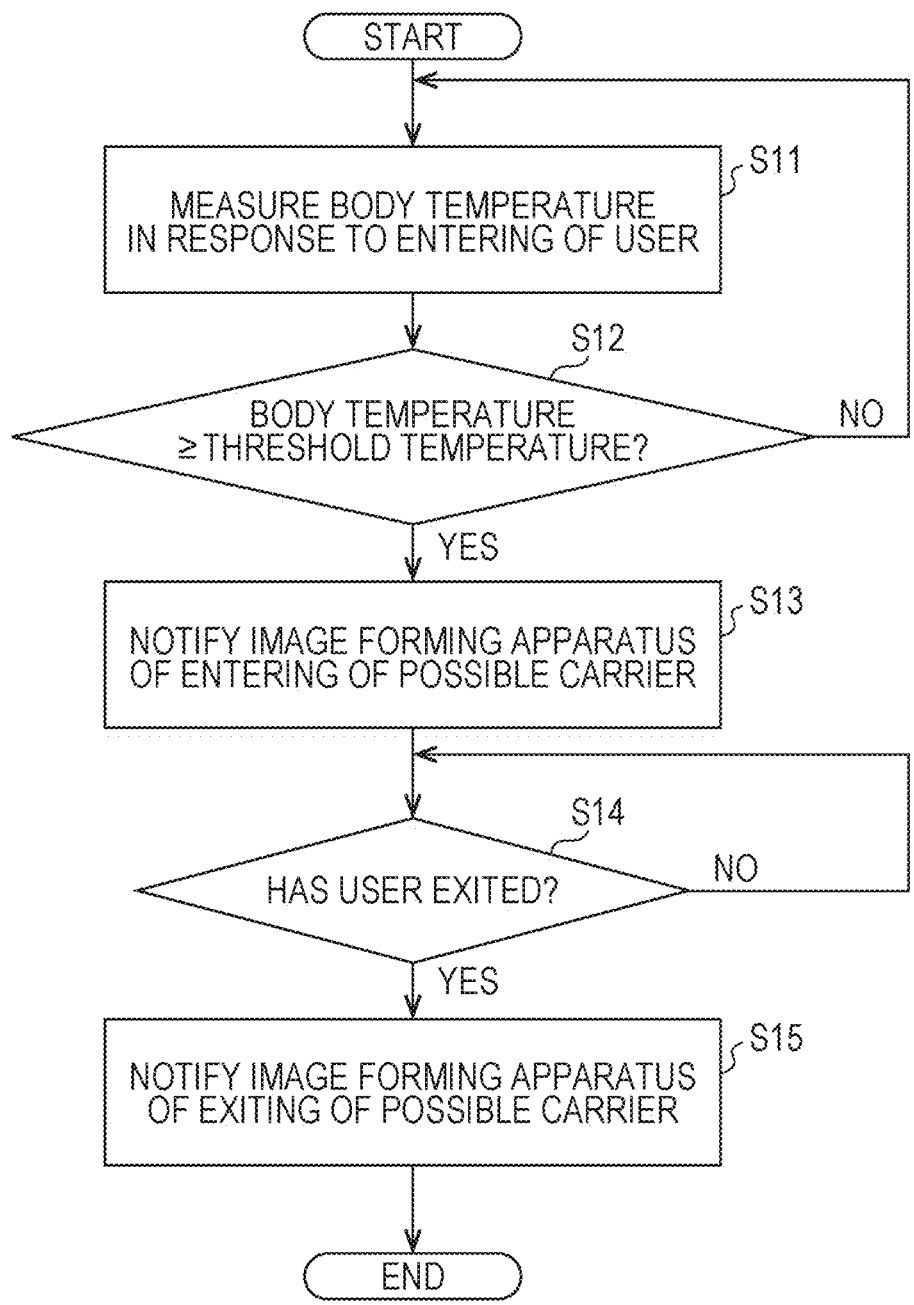

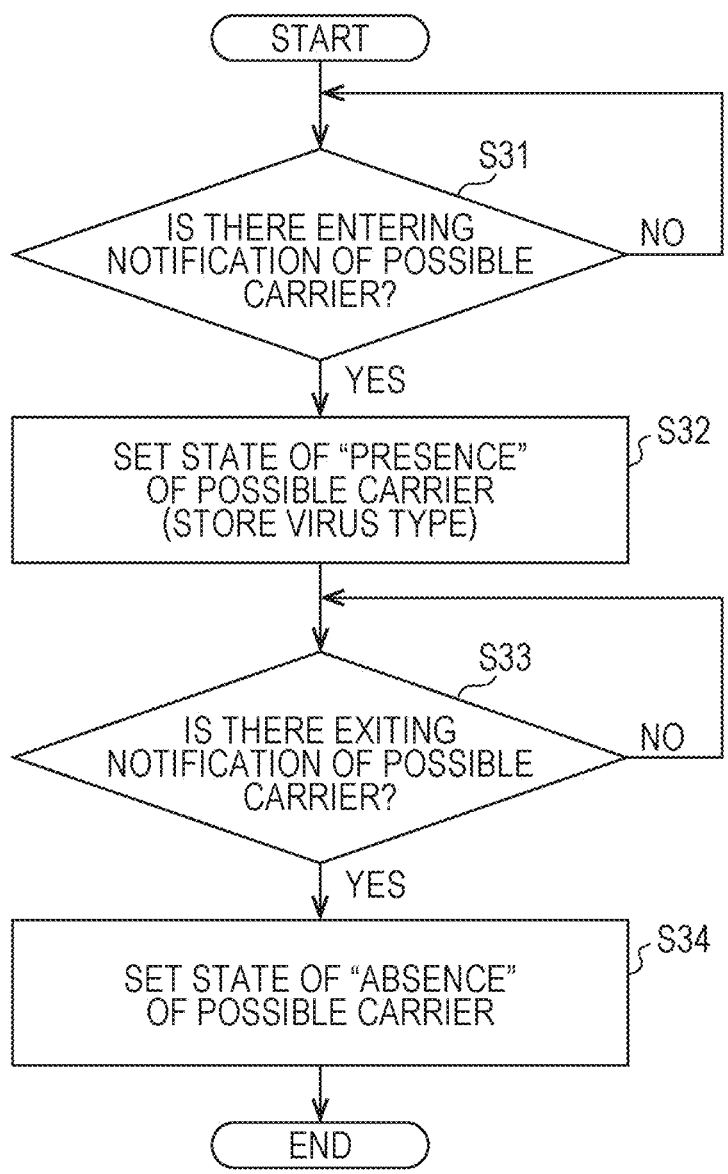

FIG. 7A

| VIRUS TYPE | VIRUS KILLING TEMPERATURE | HEAT RESISTANCE DETERMINATION |
|---|---|---|
| VIRUS A | 150°C | STRONG |
| VIRUS B | 30°C | WEAK |
| VIRUS C | 10°C | WEAK |
| VIRUS D | 200°C | STRONG |
| UNKNOWN TYPE | 200°C | STRONG (REGARDED) |

FIG. 7B

| OPERATION MODE | VIRUS HEAT RESISTANCE DETERMINATION | SHEET THICKNESS | FIXING CONDITION ||
|---|---|---|---|---|
| | | | FIXING TEMPERATURE | FIXING SPEED (CONVEYANCE SPEED) |
| VIRUS REMOVAL MODE 1 (VIA ECOLOGICAL MODE) | STRONG | THICK/THIN | 170°C | 5mm/s |
| | WEAK | THIN | 130°C | 5mm/s |
| | WEAK | THICK | 150°C | 5mm/s |
| VIRUS REMOVAL MODE 2 | STRONG/WEAK | THICK/THIN | 170°C | 5mm/s |
| NORMAL MODE | — | THICK/THIN | 200°C | 180mm/s |
| ECOLOGICAL MODE | — | THICK/THIN | 120°C | 180mm/s |

FIG. 9

| OPERATION MODE | VIRUS HEAT RESISTANCE DETERMINATION | SHEET THICKNESS | FIXING CONDITION ||||||
|---|---|---|---|---|---|---|---|
| | | | FIXING TEMPERATURE | FRONT END STOP TIME | FIXING SPEED (CONVEYANCE SPEED) | REAR END STOP TIME | HEATING SURFACE |
| VIRUS REMOVAL MODE 1 (VIA ECOLOGICAL MODE) | STRONG | THICK | 170°C | 10sec | 5mm/s | 10sec | DOUBLE SIDES |
| | | THIN | 170°C | — | 5mm/s | — | SINGLE SIDE |
| | WEAK | THICK | 150°C | 10sec | 5mm/s | 10sec | DOUBLE SIDES |
| | | THIN | 130°C | — | 5mm/s | — | SINGLE SIDE |
| VIRUS REMOVAL MODE 2 | STRONG/WEAK | THICK | 170°C | 10sec | 5mm/s | 10sec | DOUBLE SIDES |
| | | THIN | 170°C | — | 5mm/s | — | SINGLE SIDE |
| NORMAL MODE | — | THICK/THIN | 200°C | — | 180mm/s | — | SINGLE SIDE |
| ECOLOGICAL MODE | — | THICK/THIN | 120°C | — | 180mm/s | — | SINGLE SIDE |

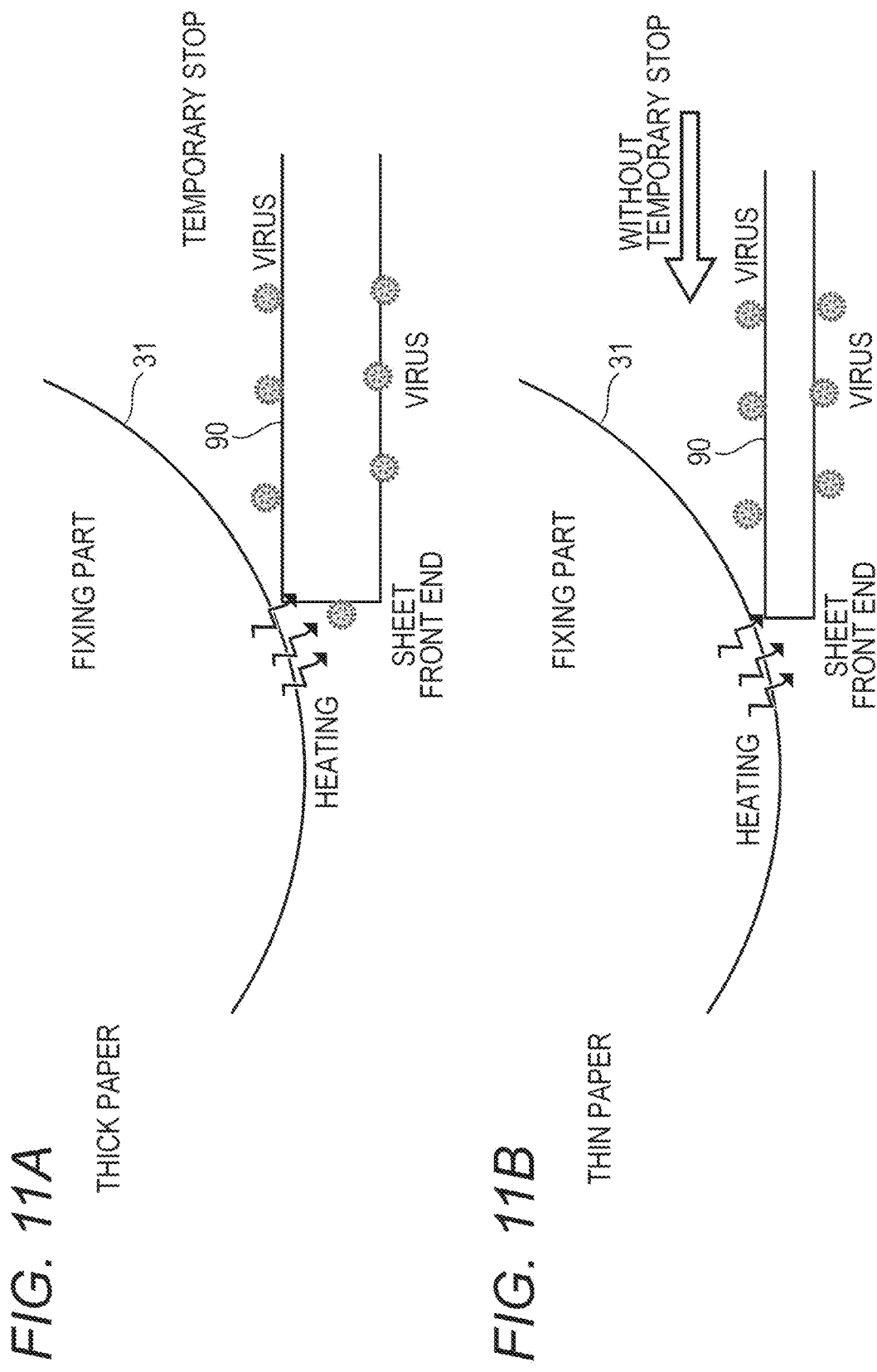

| | | |
|---|---|---|
| VIRUS A | 0–10.0°C | 200 DAYS |
| | 10.1–20.0°C | 50 DAYS |
| | 20.1–30.0°C | 20 DAYS |
| | 30.1–40.0°C | 10 DAYS |
| VIRUS B | 0–10.0°C | 300 DAYS |
| | 10.1–20.0°C | 60 DAYS |
| | 20.1–30.0°C | 30 DAYS |
| | 30.1–40.0°C | 20 DAYS |
| VIRUS C | …… | …… |
| | …… | …… |
| UNKNOWN TYPE | 0–10.0°C | 300 DAYS (REGARDED) |
| | 10.1–20.0°C | 60 DAYS (REGARDED) |
| | 20.1–30.0°C | 30 DAYS (REGARDED) |
| | 30.1–40.0°C | 20 DAYS (REGARDED) |

FIG. 15

| NUMBER | SHEET INFORMATION | | OPEN/CLOSE HISTORY | | | | | OPERATION MODE |
|---|---|---|---|---|---|---|---|---|
| | SIZE | BASIS WEIGHT | IMMEDIATELY PRECEDING REPLENISHMENT DATE AND TIME (ELAPSED TIME / REMAINING TIMER) | REPLENISHMENT IN "PRESENCE" STATE | VIRUS TYPE | APPARATUS INTERNAL TEMPERATURE | TIMER INITIAL VALUE (DISAPPEARANCE PERIOD) | |
| SHEET FEEDING TRAY 1 | A4 | THICK PAPER | 202x/09/** 10:00 (0.5 DAYS / 19.5 DAYS) | YES | VIRUS A | 21°C | 20 DAYS | VIRUS REMOVAL MODE |
| SHEET FEEDING TRAY 2 | A4 | THICK PAPER | 202x/08/** 10:00 (30 DAYS / 0 DAYS) | YES | VIRUS A | 21°C | 20 DAYS | NORMAL MODE / ECOLOGICAL MODE |
| SHEET FEEDING TRAY 3 | A4 | THIN PAPER | — | NO | — | — | — | NORMAL MODE / ECOLOGICAL MODE |
| SHEET FEEDING TRAY n | ** | ** | ** | ** | ** | ** | ** | ** |

IMAGE FORMING APPARATUS, PRINTING CONTROL METHOD, AND CONTROL PROGRAM

The entire disclosure of Japanese patent Application No. 2021-136853, filed on Aug. 25, 2021, is incorporated herein by reference in its entirety.

BACKGROUND

Technological Field

The present invention relates to an image forming apparatus, a printing control method, and a control program.

Description of the Related Art

Recently, infectious diseases caused by the novel coronavirus and the like have become a problem, and prevention of infection becomes important. When a person having a possibility of infection (hereinafter, referred to as a possible carrier) is present in a sealed room area in a building, such as an office, there is a possibility that another person is infected. In particular, when the possible carrier replenishes sheets to a sheet feeding tray of an image forming apparatus such as a printer and performs printing, there is a possibility that a virus is attached to the sheets replenished to the sheet feeding tray or the sheet feeding tray itself, and another person is infected through the sheets or the sheet feeding tray.

As a technique for removing viruses present around the apparatus, there is a technique disclosed in JP 2016-18025 A. In the electrophotographic device disclosed in JP 2016-18025 A, a fan and an adsorption decomposition catalyst (a VOC/ozone removing unit) are disposed around a fixing unit, and the adsorption decomposition catalyst decomposes and removes a volatile organic compound (VOC), bacteria, and viruses existing around an installation place.

However, in the technique of JP 2016-18025 A, even if it is possible to remove viruses and the like scattered and splashed in the air around the device, no consideration is given to removal of viruses attached to the sheets stored in the sheet feeding tray.

SUMMARY

The present invention has been made in view of the above circumstances, and an object is to provide an image forming apparatus capable of reducing a risk of infection by a virus attached to a sheet.

To achieve the abovementioned object, according to an aspect of the present invention, an image forming apparatus reflecting one aspect of the present invention comprises: one or more sheet feeding trays; an image forming part that includes a fixing part and forms an image on a sheet fed from each of the sheet feeding trays based on a print job; and an acquisition part that acquires information indicating "presence" or "absence" of a possible carrier having a possibility of virus infection in a region where an apparatus main body is installed; and a hardware processor that is able to select an operation mode of the print job from a normal mode and a virus removal mode, and sets an operation mode of the print job to the virus removal mode based on acquired information on the "presence", wherein in the virus removal mode, a fixing temperature of the fixing part is set to a predetermined temperature, and a heating time for the sheet in the fixing part is made longer than a heating time in the normal mode.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 4A is a flowchart illustrating possible carrier determination processing by a body temperature measuring device;

FIG. 5 is a flowchart illustrating state data setting processing executed by the image forming apparatus;

FIG. 7A is an example of Correspondence table 1 illustrating a relationship between virus types and heat resistance:

FIG. 7B is an example of a control table illustrating fixing conditions when a print job is executed in each operation mode:

FIG. 9 is an example of a control table illustrating fixing conditions when a print job is executed in each operation mode in a second embodiment;

FIGS. 11A and 11B are schematic views for explaining a virus killing state at a front end of a sheet;

FIG. 15 is an example of a switching table illustrating a correspondence between an open/close history and an operation mode in each sheet feeding tray;

DETAILED DESCRIPTION OF EMBODIMENTS

Figure 1:
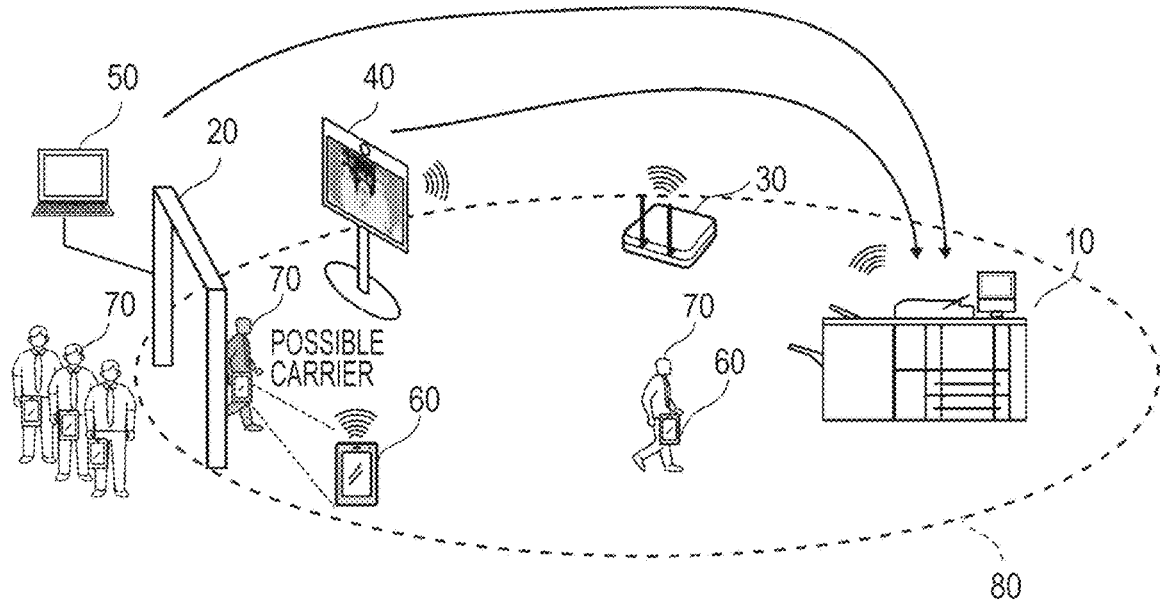
FIG. 1 is a schematic diagram illustrating an example of an image forming apparatus according to the present embodiment and a region where the image forming apparatus is installed.

Hereinafter, one or more embodiments of the present invention will be described with reference to the drawings.

However, the scope of the invention is not limited to the disclosed embodiments. In the description of the drawings, the same elements are denoted by the same reference numerals, and redundant descriptions are omitted. Further, the dimensional ratios in the drawings are exaggerated for convenience of description, and may differ from the actual ratios. In the present embodiment, a sheet includes a print sheet and various films. In particular, the print sheet includes ones produced using plant-derived mechanical pulp and/or chemical pulp. In addition, types of the sheet include gloss paper, matte paper, plain paper, high gloss paper, coated paper, and the like.

Figure 2:
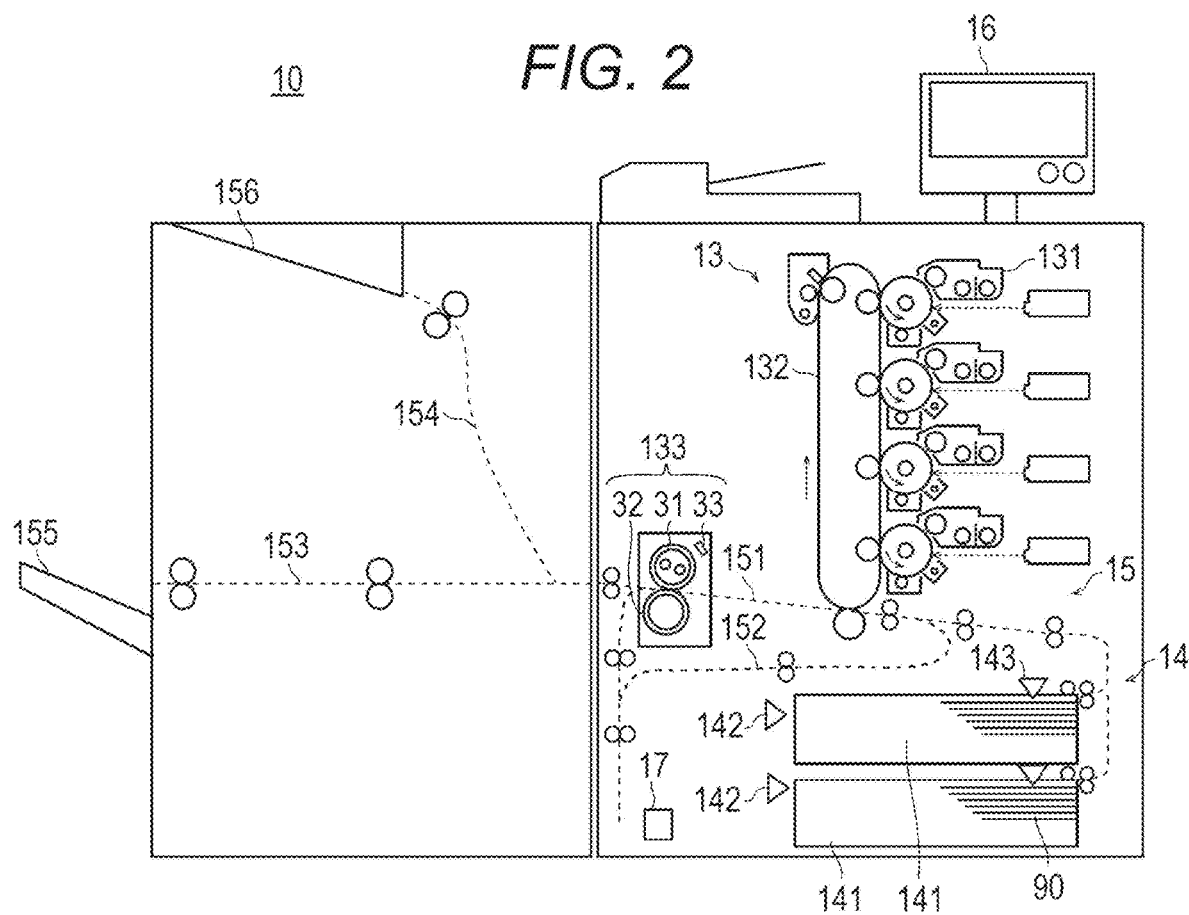
FIG. 2 is a cross-sectional view illustrating a schematic configuration of the image forming apparatus.
Figure 3:
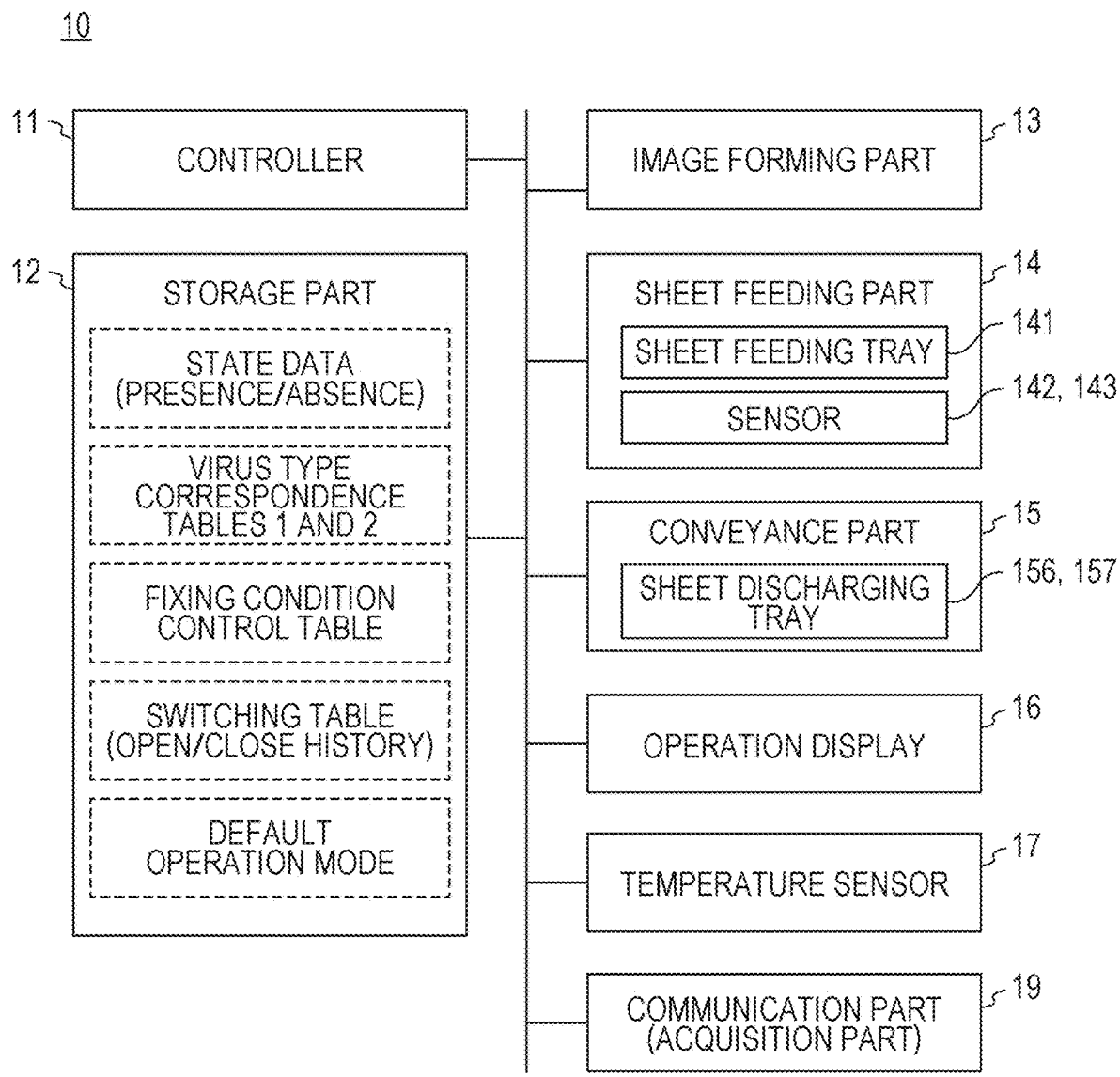
FIG. 3 is a block diagram illustrating a configuration of the image forming apparatus.

FIG. 1 is a schematic diagram illustrating an example of an image forming apparatus 10 according to the present embodiment and a region 80 where the image forming apparatus 10 is installed. FIG. 2 is a cross-sectional view illustrating a schematic configuration of the image forming apparatus 10, and FIG. 3 is a block diagram illustrating a configuration of the image forming apparatus 10.

In FIG. 1, the region 80 is a sealed region in a building, such as an office, and is one partitioned room, for example. Furthermore, the region 80 may be a plurality of partitioned regions. For example, the region 80 may be formed by a plurality of divided regions separated for each floor of a plurality of different floors, such as one entire small building.

In the region 80, the image forming apparatus 10, a gate 20, a wireless access point (AP) 30, a body temperature measuring device 40, and a terminal device 50 are disposed. In addition, in the region 80, there are employees 70 who perform work inside. Each of the employees 70 carries a portable terminal device 60 such as a smartphone.

The image forming apparatus 10 forms an image on a sheet on the basis of a received print job. Details of the image forming apparatus 10 will be described later. The gate 20 is provided at an entrance of the region 80, and authorized employees 70 alone can pass through the gate 20. The gate 20 may have a function of opening and closing a door (not illustrated) provided at the gate 20 when an employee card is held over, with use of a sensor of a near field communication (NFC) system such as FeliCa (registered trademark). Hereinafter, entry of the employee 70 into the region 80 where an apparatus main body of the image forming apparatus 10 is installed is referred to as "entering", going out is referred to as "exiting", a case where the employee 70 is present in the region 80 is referred to as "presence", and a case where the employee 70 is not present is referred to as "absence".

The wireless AP 30 is, for example, a Wi-Fi router, and relays communication between individual devices such as the terminal device 60.

(Body Temperature Measuring Device 40)

The body temperature measuring device 40 is thermography, and includes an infrared camera, a control processing part, and a display. The body temperature measuring device 40 captures an image of a person passing through the gate 20 with the infrared camera, recognizes an exposed skin part (for example, a face) of the person with image processing, and measures a body temperature of the part. On the display, an image representing a heat distribution is displayed. In this image, a numerical value indicating the body temperature of the recognized person may be displayed as an annotation. In addition, the control processing part of the body temperature measuring device 40 determines whether the body temperature is lower than a threshold temperature or equal to or higher than the threshold temperature, and outputs a determination result. For example, a person with a body temperature of 37.0° C. or higher (hereinafter, referred to as a "person with a high body temperature") is estimated to be a possible virus carrier (hereinafter, also simply referred to as a "possible carrier"). When a body temperature equal to or higher than the threshold temperature is detected, information ("presence" information of a possible carrier described later) is notified to a preset transmission destination (for example, the image forming apparatus 10). In addition, the body temperature measuring device 40 alone or in cooperation with the gate 20 specifies a person with a high body temperature, and determines entering or leaving of the specified person into or from the region 80. In a case of specifying alone, for example, the body temperature measuring device 40 includes a visible tight camera, and performs image processing on a video image thereof to recognize and specify a person entering or leaving.

(Terminal Device 50)

The terminal device 50 is, for example, a personal computer (PC) or a tablet terminal, and has a virus detection application installed therein. The terminal device 50 is installed near the gate 20. When the virus detection application detects a contact with a possible carrier, that is, when the employee 70 is a possible carrier and the portable terminal device 60 carried by the employee 70 approaches the terminal device 50, the terminal device 50 determines that the possible carrier has entered the region 80. In addition, the terminal device 50 may determine that the possible carrier has entered the region 80 in cooperation with the gate 20 having the NFC-type sensor. In this case, the terminal device 60 transmits information indicating that the employee 70 is a possible carrier and a type of the infected virus to the terminal device 50. Further, this information is transferred and notified to a preset transmission destination (for example, the image forming apparatus 10).

(Terminal Device 60)

Figure 4B:
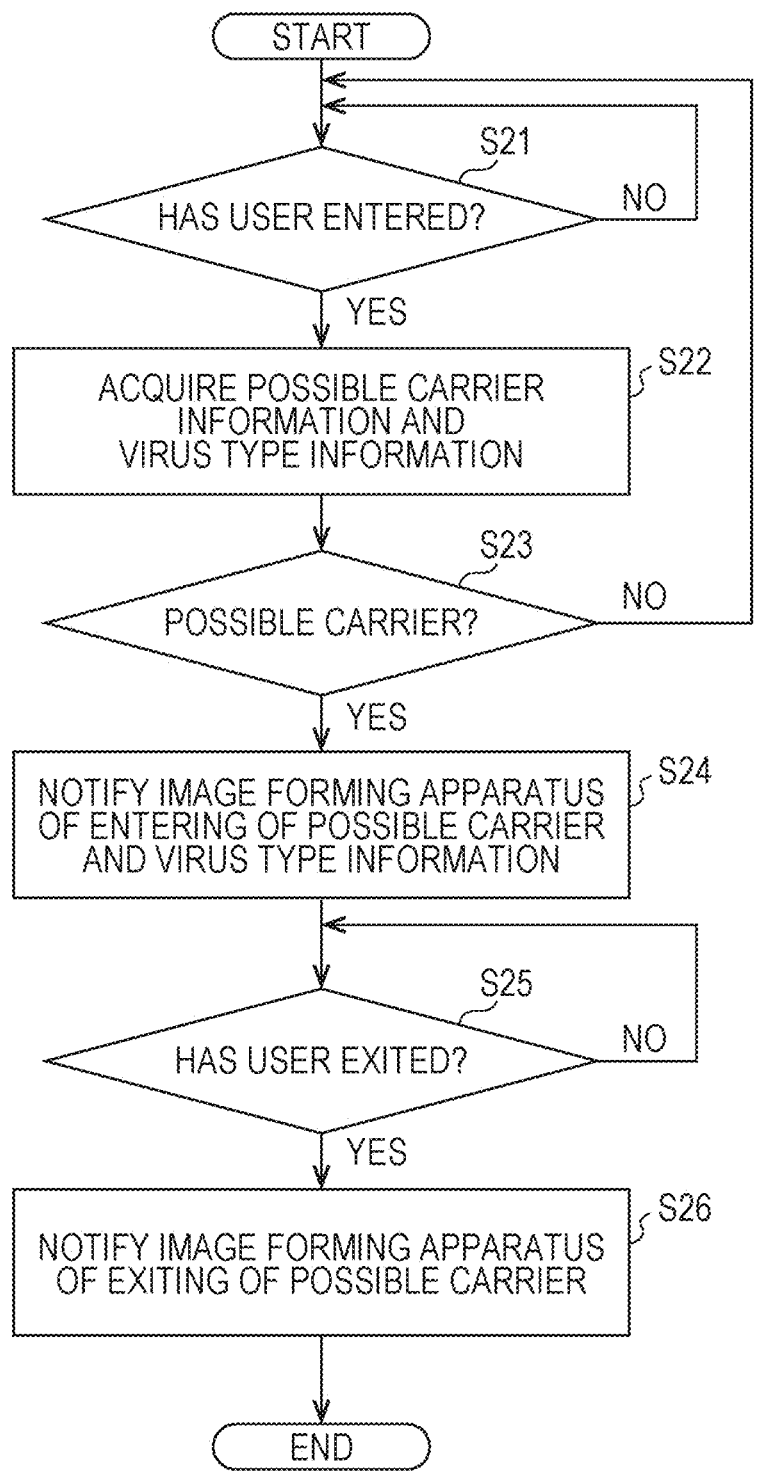
FIG. 4B is a flowchart illustrating possible carrier determination processing by a terminal device.

The terminal device 60 is a portable terminal device such as a smartphone, and has a virus detection application installed therein. The terminal device 60 holds information on whether or not a user (the employee 70) carrying the terminal device 60 is a possible carrier, and information on a virus type if necessary. The information is transmitted to the image forming apparatus 10 via the terminal device 50. Whether to be a possible carrier is determined by comparing behavior information (geographical location information) of the user carrying the terminal device 60 with behavior information of another terminal device in which identical virus detection application is installed, and determining whether the user has become a person (that is, a possible carrier) who has come into close contact with a possible carrier. In the example of FIG. 4B described above and below, an example is described in which information on entering the region 80, the possible carrier, and the virus type is notified via the terminal device 50. However, as another example, the information may be directly notified from the terminal device 60 to the image forming apparatus 10. For example, when communication of near field communication is established between the terminal device 60 and the image forming apparatus 10, the terminal device 60 notifies the image forming apparatus 10 of the information on the possible carrier and the virus type. In this case, the "the region where the apparatus main body of the image forming apparatus is installed" corresponds to a communicable range of the near field communication.

(Image Forming Apparatus 10)

Referring to FIGS. 2 and 3, the image forming apparatus 10 includes a controller 11, a storage part 12, an image forming part 13, a sheet feeding part 14, a conveyance part 15, an operation display 16, a temperature sensor 17, and a communication part 19.

The controller 11 includes a CPU and a memory. The CPU is a control circuit including a multi-core processor or the like that executes control of each part described above and various types of arithmetic processing according to a program, and each function of the image forming apparatus 10 is exerted by the CPU executing a program corresponding thereto. The memory is a high-speed accessible main storage device that stores programs and data as a work area. In addition, the controller 11 can select an operation mode of the image forming part 13 from a normal mode and a virus removal mode. Alternatively, the controller 11 can select the operation mode from the normal mode, an ecological mode, and the virus removal mode.

Figures 13, 14:
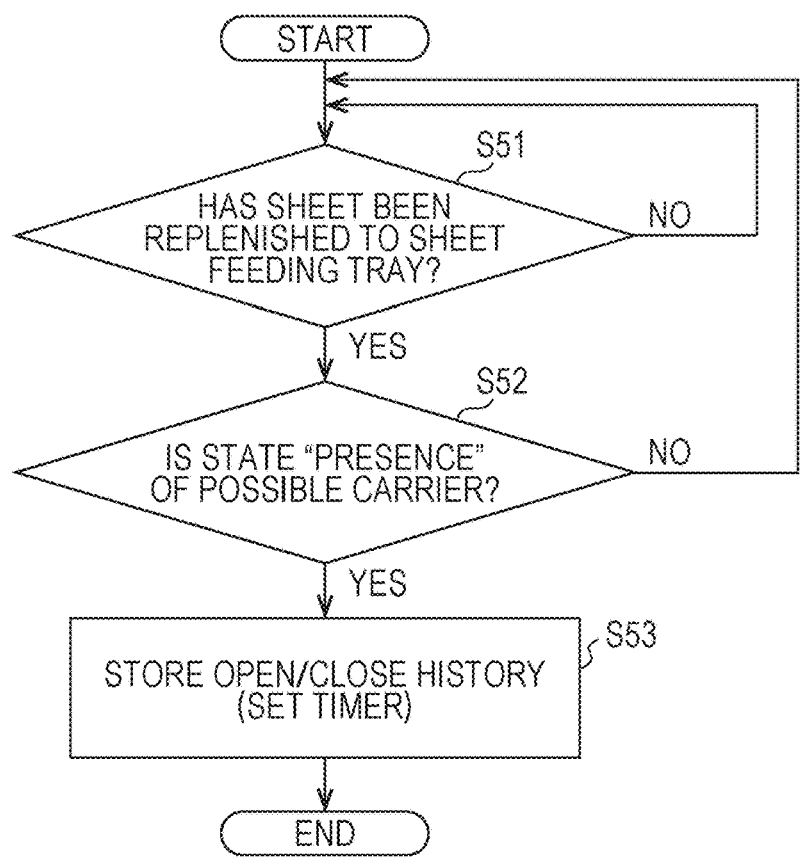
FIG. 13 is a flowchart illustrating open/close history data recording processing.
FIG. 14 is an example of Correspondence table 2 illustrating a relationship between virus types and a period until natural disappearance.

The storage part 12 is a large-capacity auxiliary storage device that stores various programs including an operating system and various data. As the storage, for example, a hard disk, a solid state drive, a flash memory, a ROM, or the like is employed. The storage part 12 stores "state data", "virus type correspondence table", "fixing condition control table", "switching table (open/close history)", and "default operation mode setting". The "state data" is information indicating a presence or absence status of a possible virus carrier in the region 80. The "virus type correspondence table" is a table indicating a relationship between virus types and heat resistance (FIG. 7A to be described later) and a table indicating a relationship between virus types and a time until natural disappearance (FIG. 14 to be described later). The "fixing condition table" is a control table that describes fixing conditions in each operation mode. The "switching table (open/close history)" describes an operation mode to be selected on the basis of an open/close history for each sheet feeding tray and an elapsed time thereof. The "default operation mode setting" is an operation mode to be executed when the virus removal mode is not executed. The user sets either the normal mode or the ecological mode with less power consumption than the normal mode.

The image forming part 13 forms an image on a sheet 90 fed from the sheet feeding part 14 and conveyed by the conveyance part 15. The image forming part 13 includes a plurality of image formation parts 131 corresponding to basic colors of Y, M, C, and K, an intermediate transfer belt 132, a fixing part 133, and the like, and forms an image on the sheet 90 by using a well-known electrophotographic imaging process including each step of charging, exposing, developing, transferring, and fixing. The fixing part 133 includes an upper roller 31, a lower roller 32, and a temperature sensor 33. Inside the upper roller 31, a heater is disposed. Power supply to the heater is controlled such that a temperature detected by the temperature sensor 33, which detects a surface temperature of the upper roller 31, becomes a predetermined fixing temperature (a control temperature). Note that a fixing bell system may be adopted as another configuration example of the fixing part 133.

The sheet feeding part 14 includes a plurality of sheet feeding trays 141. The sheet feeding tray 141 stores a plurality of sheets 90 in a state of being placed, and feeds the uppermost sheet 90 one by one. In each of the sheet feeding trays 141, an open/close sensor 142 and a sheet sensor 143 are disposed. These sensors are optical sensors or sensors combining an optical sensor and an actuator. The open/close sensor 142 detects an open/close state of the sheet feeding tray 141, that is, a state where the sheet feeding tray 141 is pulled out from the apparatus main body and a state where the sheet feeding tray 141 is loaded in the apparatus main body. The sheet sensor 143 detects the presence or absence of sheets in the sheet feeding tray 141. In response to a signal from the sheet sensor 143, the controller 11 detects that the sheets in the sheet feeding tray 141 have been used up (out of sheets) and that the sheet 90 has been replenished.

The conveyance part 15 includes conveyance paths 151 to 154, a plurality of conveyance rollers disposed in the conveyance path 151 to 154, and a drive motor (not illustrated), and conveys the sheet 90 fed from the sheet feeding tray 141 of the sheet feeding part 14. The conveyance part 15 includes sheet discharging trays 155 and 156. In accordance with setting, the controller 11 causes the sheet 90 formed with an image by the image forming part 13 to be discharged to one of the sheet discharging trays 155 and 156. When double-sided printing is to be performed, such as when print setting of a print job is set as double-sided printing, the image forming part 13 conveys the sheet 90 formed with an image on one side (a first side) to the switchback conveyance path 152. After front and back sides of the sheet 90 conveyed to the conveyance path 152 are reversed in a switchback path, the sheet 90 joins the conveyance path 151, and an image is formed on another side (a second side) of the sheet 90 again by the image forming part 13.

The operation display 16 includes a touch panel, a numeric keypad, a start button, a stop button, and the like, and is used to display various types of information and to input various instructions. Via the operation display 16, the user can set sheet information such as a size, a basis weight (a weight), and a sheet type (thick paper, thin paper, high-quality paper, and the like) of the sheets stored in each of the sheet feeding trays 141. In addition, the user can set a default operation mode through the operation display 16. For example, the operation display 16 can set the operation mode when the virus removal mode is not performed, to the normal print mode or the ecological mode. Further, as another example, the virus removal mode may be set to be forcibly executed as the operation mode (see FIG. 18 described later).

The temperature sensor 17 is disposed inside the main body of the image forming apparatus 10, and detects an internal temperature of the apparatus main body, particularly, a temperature inside or around the sheet feeding tray 141. The controller 11 refers to the temperature detected by the temperature sensor 17, and determines a period until natural disappearance of the virus (see a third embodiment to be described later).

The communication part 19 is an interface for communication with an external device. For communication, a network interface according to a standard such as Ethernet (registered trademark), SATA, PCI Express, USB, or IEEE 1394 may be used. Further, a wireless communication interface such as Bluetooth (registered trademark), IEEE 802.11, or 4G may be used for communication. The communication part 19 functions as an acquisition part in cooperation with the controller 11, and acquires information indicating "presence" or "absence" of a possible carrier and/or information on the virus type, from the body temperature measuring device 40 or the terminal device 50.

(Setting Processing for State Data on Presence/Absence of Possible Virus Carrier)

Next, with reference to FIGS. 4A, 4B, and 5, state data holding processing will be described.

FIG. 4A is a flowchart illustrating possible carrier determination processing by the body temperature measuring device 40. FIG. 4B is a flowchart illustrating possible carrier determination processing by the terminal device 50. FIG. 5 is a flowchart illustrating state data setting processing executed by the image forming apparatus 10.

(Determination Processing by Body Temperature Measuring Device 40)

(Step S11)

Here, the body temperature measuring device 40 captures, with an infrared camera, an image of a user (the employee 70) who passes through the gate 20 to enter, and measures a body temperature of the user (the employee 70).

(Step S12)

When the measured body temperature is equal to or higher than a threshold temperature (for example, 37.0° C. or higher), the process proceeds to step S13. When the measured body temperature is lower than the threshold value, the process of step S11 is repeated.

(Step S13)

The body temperature measuring device 40 notifies the image forming apparatus 10 that a person with a high body temperature, that is, a possible carrier has entered.

(Step S14)

The body temperature measuring device 40 determines whether the possible carrier has exited. For example, by the visible light camera of the body temperature measuring device 40, images of a user who enters and a user who exits are individually captured, and a person who is determined as a person with a high body temperature at the time of entering and determined to be a possible carrier is stored. Then, when it is determined that the same person has exited, it is determined that the possible carrier has exited. When the possible carrier has exited (YES), the process proceeds to step S15.

(Step S15)

Here, the body temperature measuring device 40 notifies the image forming apparatus 10 of the exiting of the possible carrier.

(Determination Processing by Terminal Device 50)

(Steps S21 and S22)

In response to entering of the user (the employee 70), the terminal device 50 acquires possible carrier information and virus type information from the terminal device 60 carried by the user.

(Step S23)

When the information acquired in step S22 has contents indicating that the user carrying the terminal device 60 is a possible carrier (YES), the process proceeds to step S24.

(Step S24)

The terminal device 50 notifies the image forming apparatus 10 of the fact that possible carrier has entered and information on the virus type.

(Step S25)

When the same user (the terminal device 60 having the same ID) determined to be a possible carrier in step S23 has passed, the terminal device 50 determines that the user determined to be a possible carrier has exited (YES).

(Step S26)

Here, the terminal device 50 notifies the image forming apparatus 10 of the exiting of the possible carrier.

(State Data Setting Processing by Image Forming Apparatus 10)

(Step S31)

When the controller 11 of the image forming apparatus 10 receives an entering notification of a possible carrier (YES), the process proceeds to step S32. This notification corresponds to "information on "presence" of a possible carrier having a possibility of virus infection" (hereinafter, also simply referred to as "presence" or information on "presence"), which has been transmitted by the process in step S13 of the body temperature measuring device 40 or the process in step S24 of the terminal device 50, for example.

(Step S32)

The controller 11 updates state data stored in the storage part 12 to a status of "presence". Further, if information on a virus type is also obtained in step S31 (for example, step S24 of the terminal device 50), the information on the virus type is stored together as the state data. As will be described later, when the state data is the status of "presence", the controller 11 operates a print job to be executed in the virus removal mode.

(Step S33)

When the controller 11 of the image forming apparatus 10 receives an exiting notification of a possible carrier (YES), the process proceeds to step S34. This notification corresponds to "information on "absence" of a possible carrier having a possibility of virus infection", which has been transmitted by the process in step S15 of the body temperature measuring device 40 or the process in step S26 of the terminal device 50, for example.

(Step S34)

The controller 11 updates state data stored in the storage part 12 to a status of "absence". Note that, in a case where information on "presence" is simultaneously acquired from a plurality of devices (for example, the body temperature measuring device 40 and the terminal device 50), the state data is to be set to "absence" when all the information is set to "absence".

(Print Control Processing in First Embodiment)

Figure 6:
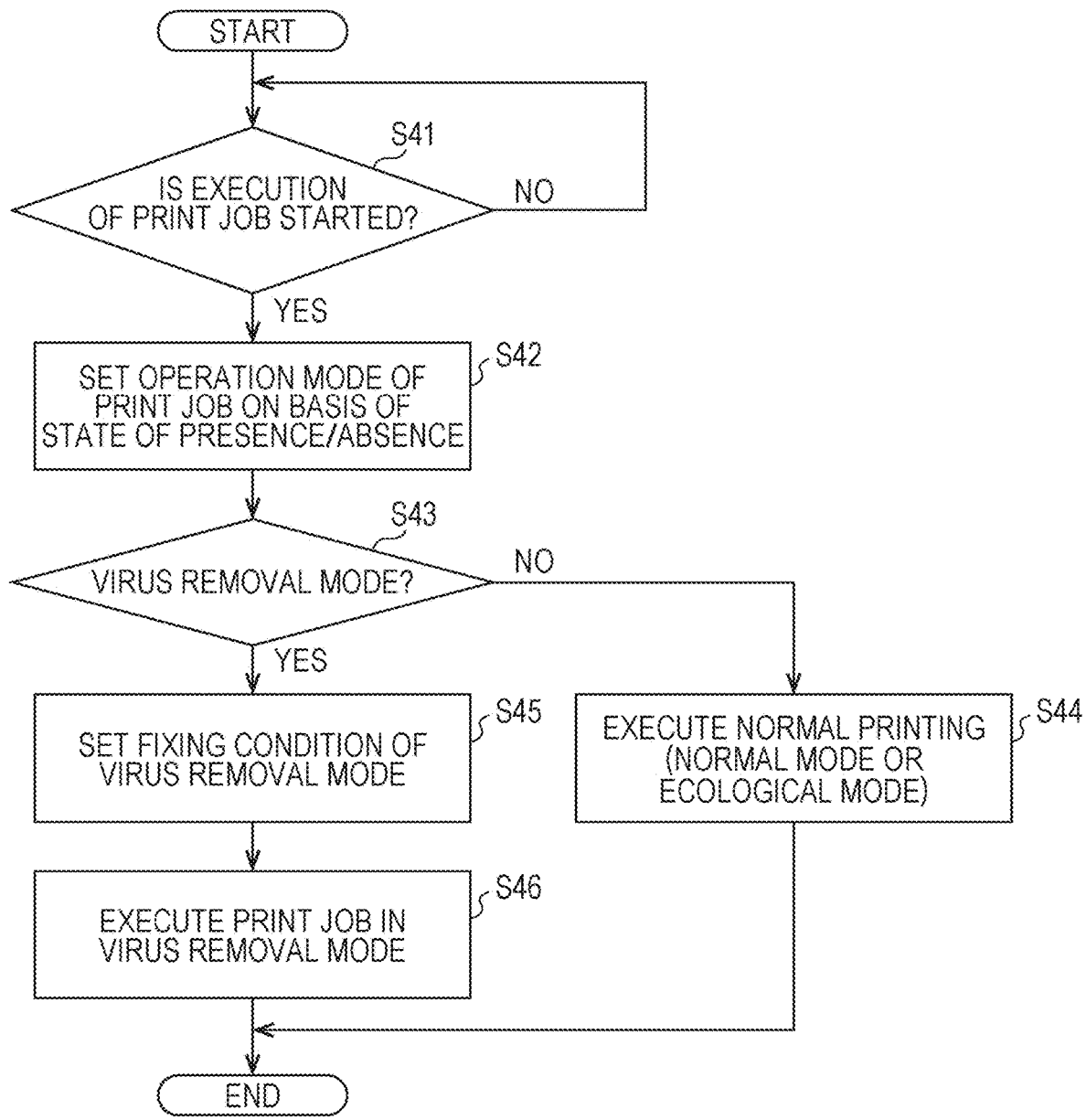
FIG. 6 is a flowchart illustrating print control processing in a first embodiment.
Figure 8:
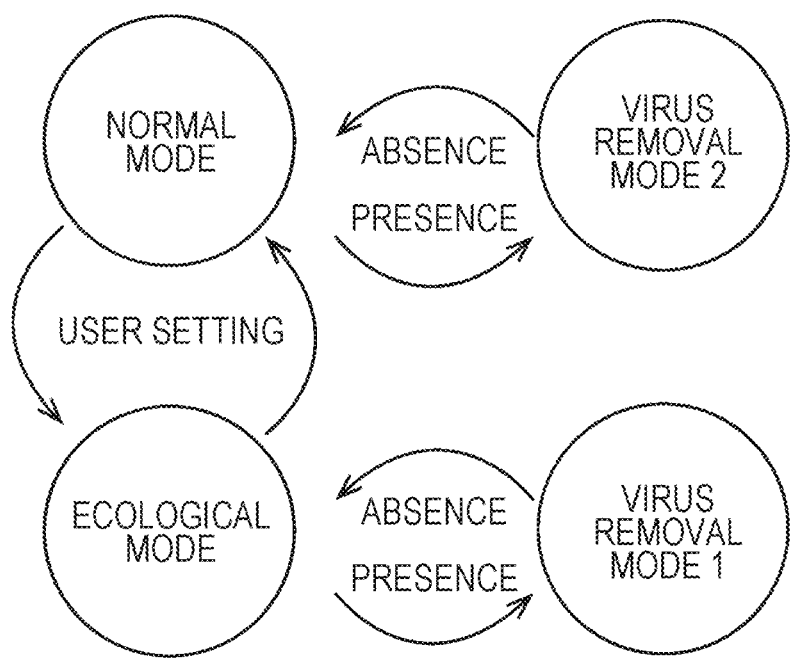
FIG. 8 is a view illustrating state transition of each operation mode.

Next, with reference to FIGS. 6 to 8, print control processing will be described. FIG. 6 is a flowchart illustrating print control processing according to a first embodiment.

(Step S41)

When the controller 11 receives a print job from an external PC, or by a start button being pressed or the like (YES), the process proceeds to step S42. Data of the received print job includes a job ticket (print setting information) and print data (image data). In the job ticket, print settings are described, such as a sheet to be used (a sheet feeding tray), a sheet size, a sheet basis weight or a sheet type, single-sided/double-sided printing, and a color mode.

(Step S42)

The controller 11 determines an operation mode on the basis of presence/absence information of state data stored in the storage part 12. This state data has been set by the setting processing in FIG. 5 described above. When the state data is "presence", that is, when a possible virus carrier is present in the region 80, the controller 11 sets the operation mode to the virus removal mode. Whereas, when the state data is "absence", that is, when there is no possible virus carrier in the region 80, an operation mode (the normal mode or the ecological mode) according to the setting of the default operation mode stored in the storage part 12 is set.

(Step S43)

When the set operation mode is not the virus removal mode (NO), the controller 11 advances the process to step S44. Whereas, when the virus removal mode is set (YES), the process proceeds to step S45.

(Step S44)

Here, the controller 11 executes normal printing in the default operation mode (the normal mode or the ecological mode). Fixing conditions of the operation mode (the normal mode or the ecological mode) in the normal printing are as illustrated in FIG. 7B described later.

(Step S45)

Here, the controller 11 sets fixing conditions of the virus removal mode. Here, with reference to FIGS. 7A to 8, a fixing condition setting method will be described. FIG. 7A is an example of a correspondence table (Correspondence table 1) indicating a relationship between virus types and heat resistance, and FIG. 7B is an example of a control table indicating fixing conditions when a print job is executed in each operation mode. FIG. 8 is a view illustrating state transition of each operation mode.

(Fixing Condition Setting)

As illustrated in FIG. 7A, virus killing temperatures are different for viruses depending on the virus type. Here, the virus killing, temperature is a fixing temperature, and is determined by the following formula. Virus killing temperature=killing temperature assumed for each virus (heating at a certain temperature x or higher is required)+ margin (a margin for ensuring reliable heating at the temperature x or higher).

In addition, in FIG. 7A, the heat resistance is classified into a plurality of ranks according to the virus killing temperature. For example, viruses A and D are classified as "strong" in the heat resistance determination since the virus killing temperature is high, and viruses B and C are classified as "weak" in the heat resistance determination since the virus killing temperature is low. Note that the classification is not limited to two stages, and classification may be made into three or more stages. Note that, a case is also assumed in which there is information on "presence" alone and there is no virus type information, even when the notification is made from the body temperature measuring device 40 (step S13) or when the notification is made from the terminal device 50 (step S24). In such a case where the virus type is an "unknown type", a value of the virus type under the strictest condition for the virus killing temperature is used, and the heat resistance determination is regarded as "strong".

The fixing condition in the virus removal mode is set based on virus heat resistance determination and a sheet thickness by using the control table illustrated in FIG. 7B. The sheet thickness has been determined based on the sheet type or the sheet basis weight described in the job ticket of the print job. For example, in a case of the sheet basis weight, a sheet of 200 g/m² or more is determined to be thick paper. Further, in the determination as thick paper, in a case where the image forming apparatus 10 includes a medium sensor that measures characteristics of the sheet on the conveyance path, a sheet having a predetermined thickness or more may be determined as thick paper in accordance with a sheet thickness measured by the medium sensor. Sheets other than the thick paper, including plain paper and thin paper, are classified as thin paper in the control table of FIG. 7B.

Here, in the present embodiment, as illustrated in FIG. 7B, there are two virus removal modes: Virus removal mode 1 via the ecological mode; and Virus removal mode 2 via the normal mode. As illustrated in a state transition view of FIG. 8, the setting between the normal mode and the ecological mode is set by the user (the default operation mode setting described above). Then, when the default operation mode is the ecological mode, the operation mode transitions to Virus removal mode 1 in accordance with the information on "presence". Whereas, when the default operation mode is the normal mode, the operation mode transitions to Virus removal mode 2 in accordance with the information on "presence".

For example, as illustrated in FIG. 7B, when the virus heat resistance determination is "strong" in Virus removal mode 1, regardless of the thickness of the sheet (common for thick paper and thin paper), the fixing temperature is set to a predetermined temperature of 170° C., and a conveyance speed (hereinafter, also referred to as a "fixing speed") of the sheet 90 in the fixing part 133 is set to 5 mm/s. As illustrated in FIG. 7B, the fixing temperature in the virus removal mode (Virus removal modes 1 and 2) is higher than 120° C. in the ecological mode. In addition, since the fixing speed 5 mm/s in the virus removal mode is lower than the fixing speed 180 mm/s in the normal mode (and the ecological mode), a heating time for the sheet 90 by the fixing part 133 becomes long.

(Step S46)

Here, the controller 11 controls the image forming part 13 to execute the print job in the virus removal mode with the fixing conditions set in step S45.

As described above, the image forming apparatus according to the present embodiment includes the controller that can select the operation mode of a print job from the normal mode and the virus removal mode, and sets an operation mode of the print job to the virus removal mode on the basis of acquired information of the "presence". In the virus removal mode, the fixing temperature of the fixing part is set to a predetermined temperature, and a heating time for the sheet in the fixing part is made longer than that in the normal mode. This makes it possible to appropriately remove the virus attached to the sheet and to reduce the risk of virus infection. In addition, the image forming apparatus according to the present embodiment sets the fixing temperature according to the type of the acquired virus. This enables the virus to be more appropriately removed.

Second Embodiment

Next, with reference to FIGS. 9 to 11B, an image forming apparatus 10 according to a second embodiment will be described. In the first embodiment, the heating time for the sheet in the fixing part in the virus removal mode is made longer than that in the normal mode, by uniformly reducing the fixing speed on the entire surface of the sheet 90. However, as described in the second embodiment below, the heating time may be made longer than that in the normal mode by further reducing the fixing speed or performing double-sided heating (heating twice) at a front end/rear end of the sheet. Other configurations than those illustrated in these figures are the same as those of the image forming apparatus 10 of the first embodiment illustrated in FIGS. 1 to 8, and the description thereof will be omitted. FIG. 9 is an example of a control table illustrating fixing conditions when a print job is executed in each operation mode in the second embodiment. This control table is applied in step S45 of FIG. 6. In the control table in the second embodiment illustrated in FIG. 9, a heating surface and a fixing speed of the front end/rear end are different from those of the control table (FIG. 7B) in the first embodiment.

(Heating Surface (Double-Sided Heating))

Here, the heating surface in the control table illustrated in FIG. 9 indicates a heating surface when a print setting is single-sided printing, and indicates that double-sided heating is performed when the heating surface is "double side" even if the print setting is single-sided printing. Here, the double-sided heating means that printing on one side (a first side) is performed as usual, heating is performed by a fixing part 133, the sheet passes through a switchback conveyance path 152 and a conveyance path 151, and then second heating is performed by the fixing part 133. Note that, when the sheet passes through the conveyance path 151 for the second time, image formation is not performed by an image forming part 13 (blank data).

Figure 10A:
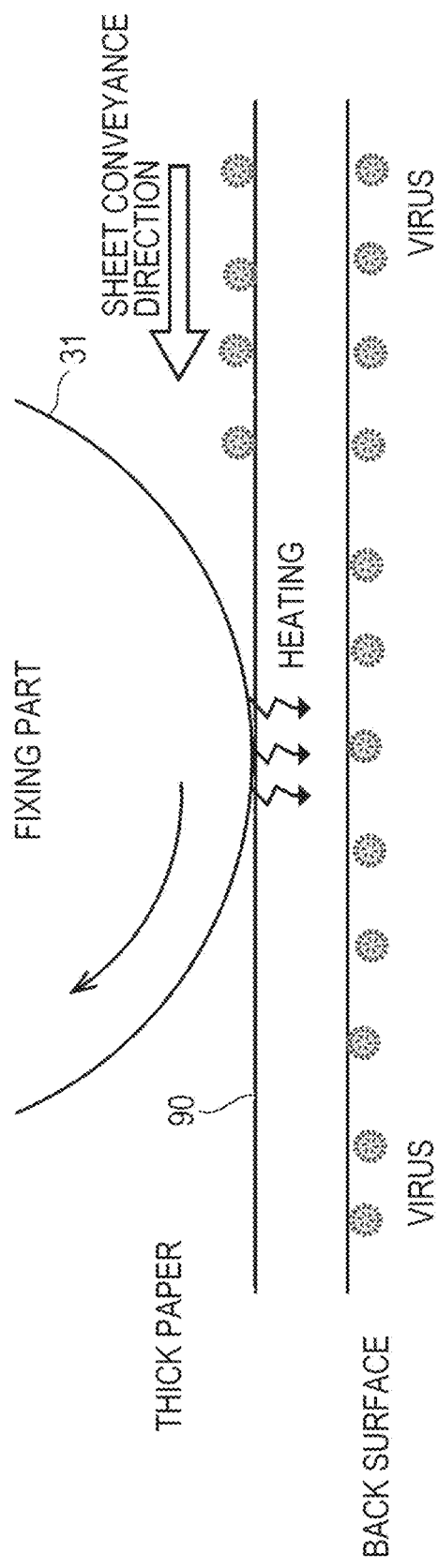
FIGS. 10A and 10B are schematic views for explaining a virus killing state in single-sided printing.
Figure 10B:
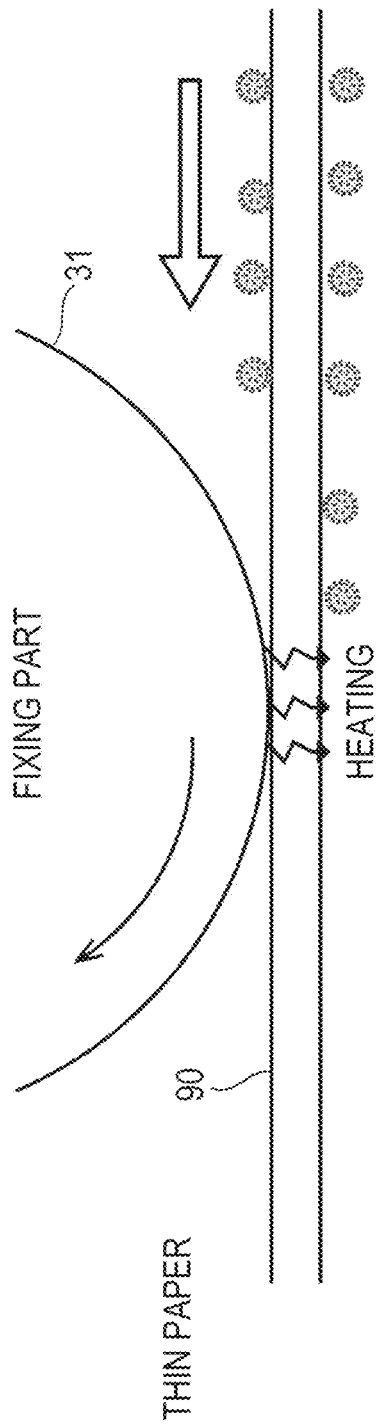

In the control table illustrated in FIG. 9, in a virus removal mode, in a case of thick paper, double-sided heating is executed even if the print setting is single-sided printing. FIGS. 10A and 10B are schematic views for explaining a virus killing state in single-sided printing. In a case of thick paper as illustrated in FIG. 10A, there is a high possibility that it is not possible to sufficiently heat a virus attached to a back surface side of a sheet 90 with one-time heating by single-sided printing, and the virus remains without being killed. Therefore, in the second embodiment, double-sided heating is performed in the case of thick paper. Whereas, in a case of thin paper (other than thick paper) as illustrated in FIG. 10B, it is possible to sufficiently heat both sides of the sheet 90 by one-time heating, and the virus can be removed. When the original print setting is double-sided printing, double-sided printing (double-sided heating) is naturally performed without distinction between thin paper and thick paper.

(Reduction of Fixing Speed or Temporary Stop at Sheet End Part)

In addition, in the second embodiment, a fixing speed at an end part of a front end and/or a rear end of the sheet 90 is made slower than a fixing speed at a center of the sheet. In the present embodiment, the sheet end part includes a range of several mm before and after the sheet end part passes through a fixing nip formed by the upper and lower rollers 31 and 32. Further, making the fixing speed slower than that at the center means, for example, setting the fixing speed within a speed range of 80% to 0% of the fixing speed (5 mm/s) at the center. In the example illustrated in the control table of FIG. 9, the fixing speed is set to zero (temporary stop) near the end parts of both end parts of the front end and the rear end of the sheet 90. The temporary stop time is 10 sec. For example, when the front end of the sheet 90 reaches the fixing nip of the fixing part 133, driving rotation of the fixing part 133 is stopped in a range of several mm in the front-back direction as the vicinity of the end part, and the fixing part 133 is driven again after 10 sec elapses. The same processing is also performed on the rear end of the sheet 90.

FIGS. 11A and 11B are schematic views for explaining a virus killing state at the front end of the sheet. In a case of thick paper as illustrated in FIG. 11A, there is a high possibility that it is not possible to sufficiently heat a virus attached to an end face at the front end of the sheet 90, and the virus remains without being killed. Therefore, in the present embodiment, in the case of thick paper, the heating of the end face is sufficiently performed by temporarily stopping the sheet. Note that, in a case where double-sided heating is performed without formation of an image (blank data) on the second surface, the heating of the end face is preferably performed at a time of the second heating without formation of an image. Furthermore, if a timing of the temporary stop is during image formation by the image forming part 13 (during a process of exposure, primary transfer, and secondary transfer) under conditions such as double-sided printing and a case where a sheet length of the sheet 90 is long, the temporary stop processing may be performed on the rear end side alone.

As described above, in the second embodiment, the virus attached to the end face of the sheet 90 can be removed by making the fixing speed slower at the end part of the front end and/or the rear end of the sheet than that at the center.

Third Embodiment

Next, with reference to FIGS. 12 to 17, an image forming apparatus 10 according to the third embodiment will be described. Other configurations than those illustrated in these figures are the same as those of the image forming apparatus 10 of the first and second embodiments illustrated in FIGS. 1 to 9, and the description thereof will be omitted. In the first and second embodiments, whether or not the virus removal mode can be executed is determined on the basis of information on presence of a possible carrier or absence of a possible carrier in the region 80. In the third embodiment to be described below, whether or not the virus removal mode can be executed is determined in consideration of an influence of a case where a possible carrier touches a sheet feeding tray 141 and a sheet 90 therein.

Figure 12:
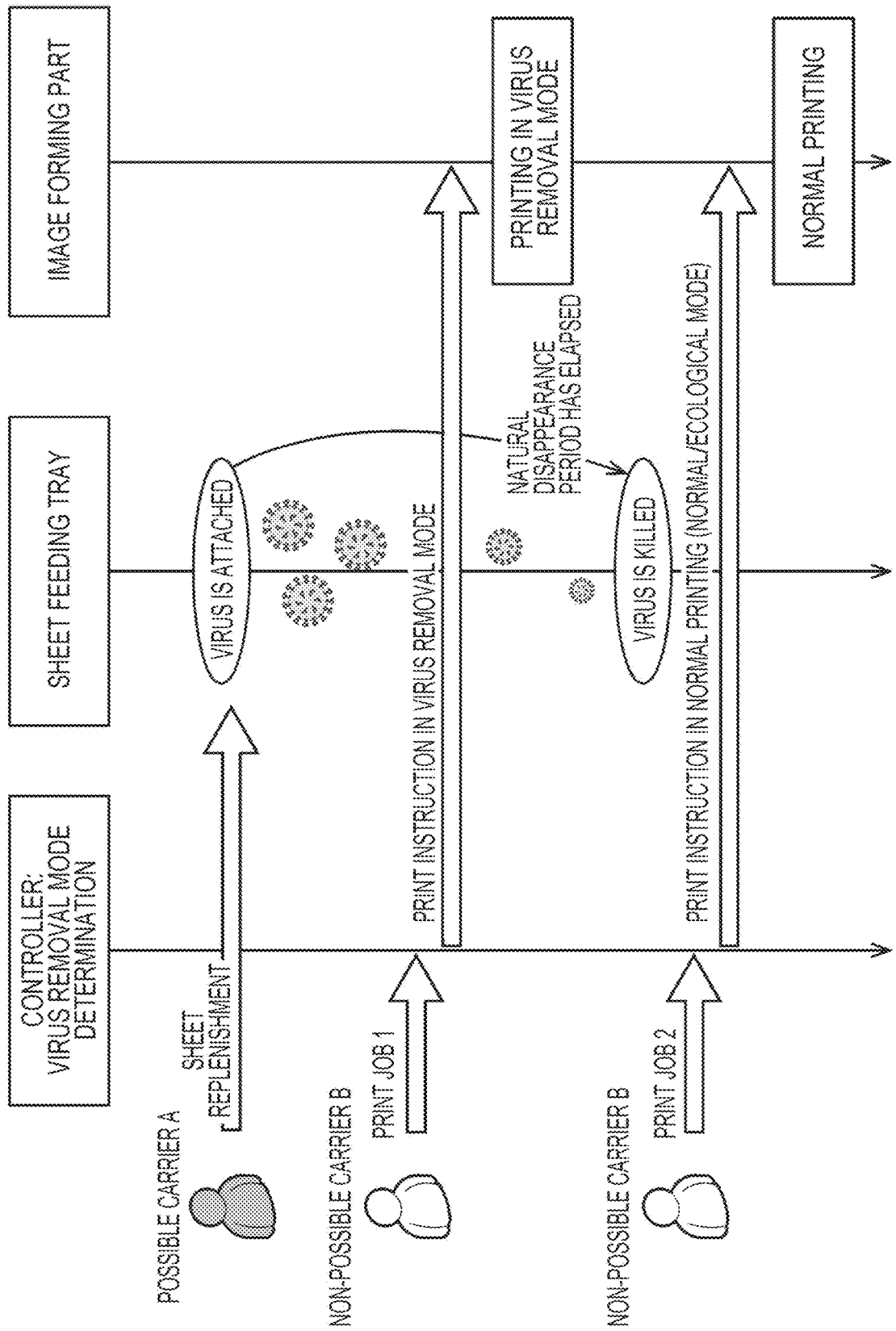
FIG. 12 is a schematic view illustrating a relationship between an elapsed time after a sheet is replenished to a sheet feeding tray and an operation mode to be set, according to a third embodiment.

FIG. 12 is a schematic view illustrating a relationship between an elapsed time after a sheet is replenished to a sheet feeding tray and an operation mode to be set, according to the third embodiment. When a possible carrier (hereinafter, referred to as a possible carrier A) replenishes the sheet 90 to the sheet feeding tray 141, a virus is attached to the sheet feeding tray 141 and the sheet 90 therein. The attached virus is not immediately killed, and continues to be present within a certain period. When another user (hereinafter, referred to as a non-possible carrier B) issues a print instruction for a print job 1 within the certain period, an image forming part 13 executes printing in the virus removal mode. Whereas, when a certain period of time (hereinafter, referred to as a disappearance period) has elapsed after the sheet replenishment by the possible carrier A, the virus has been naturally killed, so that the image forming part 13 executes normal printing with higher productivity when the non-possible carrier B instructs printing of a print job 2. The above is an outline of control in the third embodiment. How to actually perform the control will be described below.

FIG. 13 is a flowchart illustrating open/close history data recording processing.

(Step S51)

A controller 11 determines whether or not sheet replenishment to the sheet feeding tray 141 has been performed. This determination may be made on the basis of a signal of an open/close sensor 142 indicating that an open/close operation of the sheet feeding tray 141 is performed, on the basis of a signal from the sheet sensor 143 indicating that the sheet in the sheet feeding tray 141 is changed from an absent state to a present state, or on the basis of a combination of both signals. When the controller 11 determines that sheet replenishment has been performed, the process proceeds to step S52.

(Step S52)

The controller 11 determines an operation mode on the basis of presence/absence information of state data stored in a storage part 12. This state data has been set by the setting processing in FIG. 6 described above. When the status is "presence" indicating that a possible carrier is present in the region 80 (YES), the process proceeds to step S53, and when the status is "absence" (NO), the process returns to step S51. In the present embodiment, it is not specified whether or not the possible carrier and the user who has replenished in step S51 are the same person. However, the image forming apparatus 10 side may have a function of specifying a user who uses the image forming apparatus 10 (authentication processing of the user, or the like), so that the present processing may be executed when a possible carrier performs replenishment.

(Step S53)

The controller 11 records the open/close history into the storage part 12. At this time, an initial value (the disappearance period) of a timer is set. FIG. 14 is an example of a correspondence table (Correspondence table 2) indicating a relationship between virus types and a time until natural disappearance. A virus generally disappears after a certain period (the disappearance period) elapses, but the disappearance period varies depending on a virus type and an environmental temperature. As illustrated in Correspondence table 2 in FIG. 14, a period after separation from a carrier before natural disappearance is longer as the environmental temperature is lower. In addition, the period to the natural disappearance varies depending on the type, and is longer for the virus B than the virus A. Note that it is also assumed that state data includes information on "presence" alone and does not include information of a virus type. As illustrated in FIG. 14, when the virus type is an "unknown type", a value of the virus type under the strictest condition is used (regarded).

FIG. 15 is an example of a switching table illustrating a correspondence between an open/close history and an operation mode in each sheet feeding tray. The switching table is set for each sheet feeding tray 141, and includes sheet information, an open/close history, and an operation mode.

The sheet information includes a sheet size, and a basis weight or a sheet type. The example of FIG. 15 illustrates that a sheet feeding tray 1 stores A4 size thick paper.

The open/close history includes immediately preceding replenishment date and time, information indicating whether or not the replenishment is replenishment in the "presence" state (corresponding to steps S51 and S52), a virus type, an internal temperature of the apparatus at a time of replenishment, and a timer initial value. The timer initial value is set at a time of replenishment in accordance with Correspondence table 2 of FIG. 13 and the internal temperature at that time (corresponding to step S53). For example, at the time of replenishment, if a possible carrier is "presence", the type is the virus A, and a temperature detected by a temperature sensor 17 is 21° C., the controller 11 sets 20 days as the timer initial value (a killing period) with reference to FIG. 13.

The operation mode is determined based on the remaining timer. In the example illustrated in FIG. 15, since the elapsed time from the replenishment of the sheet feeding tray 1 is 0.5 days and the remaining timer is 19.5 days, the operation mode is the virus removal mode. Since the elapsed time from the replenishment of a sheet feeding tray 2 is 30 days and the remaining timer is 0 days, the virus removal mode is not applied, and the operation mode is a normal mode or an ecological mode according to the user's setting. Since a sheet feeding tray 3 is not in the "presence" state at the time of replenishment, the virus removal mode is not applied regardless of the elapsed time, and the operation mode is the normal mode or the ecological mode according to the user's setting.

(Print Control Processing in Third Embodiment)

Figure 16:
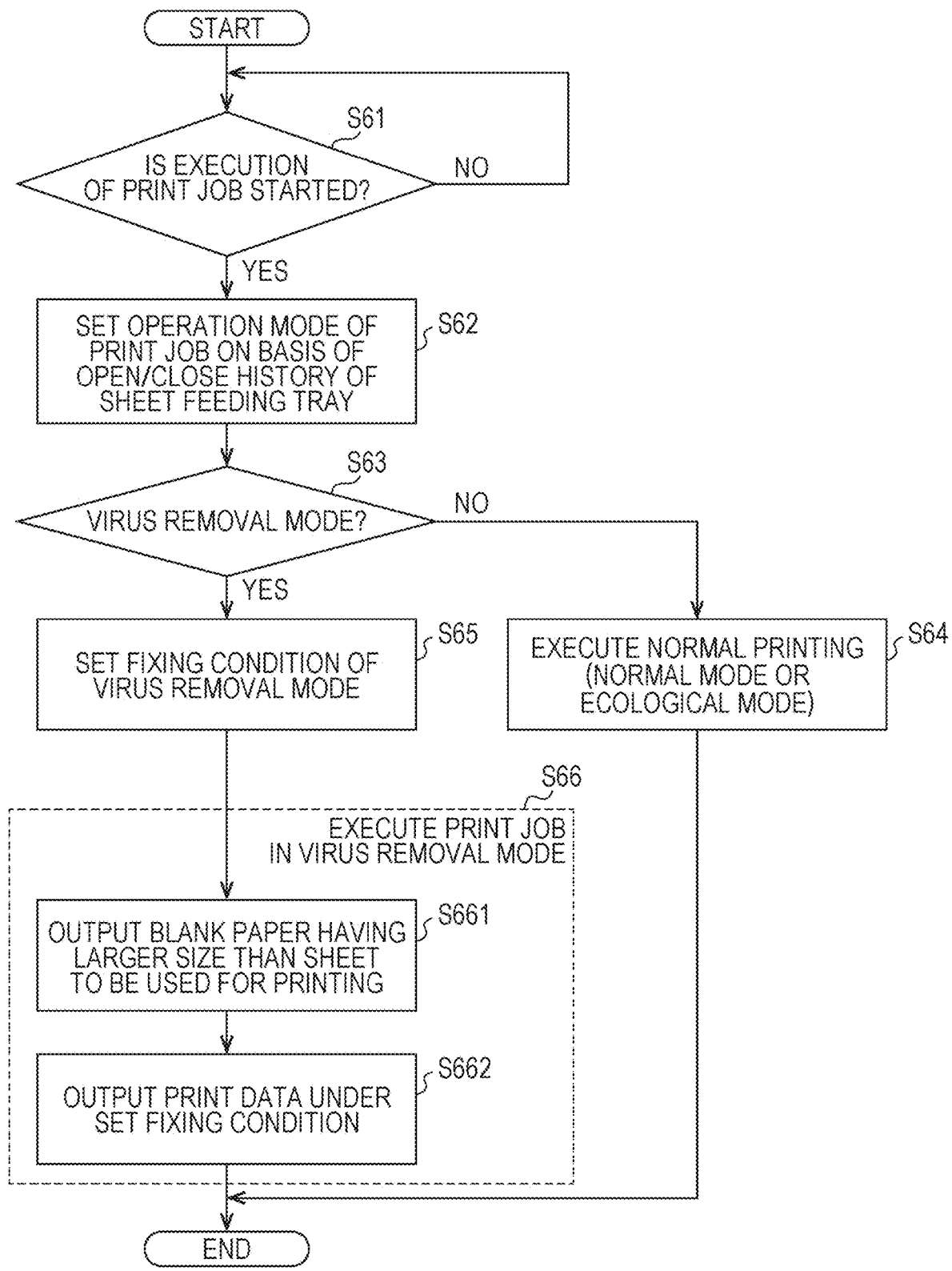
FIG. 16 is a flowchart illustrating print control processing in the third embodiment.

Next, with reference to FIGS. 16 and 17, print control processing will be described. FIG. 16 is a flowchart illustrating print control processing in the third embodiment.

(Step S61)

When receiving a print job (YES), the controller 11 advances the process to step S62.

(Step S62)

The controller 11 determines the operation mode on the basis of the open/close history of the sheet feeding tray. The operation mode is determined with reference to the switching table in FIG. 15. The operation mode in this switching table has been determined on the basis of, as described above, the sheet replenishment date and time of the sheet feeding tray, information indicating whether or not the replenishment at that time is replenishment in the "presence" state (corresponding to steps S51 to S52), the virus type, the internal temperature of the apparatus at the time of replenishment, and the elapsed time (the remaining timer).

(Steps S63 to S65)

The process here is the same as steps S43 to S45 in FIG. 6, and the description thereof will be omitted.

(Step S66)

Here, the print job is executed in the virus removal mode. When this print job is executed, blank paper having a larger size than the sheet to be used in this output is outputted before the first output (a product output) of the print data (step S661). For example, when the sheet size described in the job ticket is A4, a sheet having a larger size, for example, A3 or B4 size over the described sheet size is outputted as blank paper. Although a plurality of sheets of blank paper may be outputted, it is preferable to output one sheet alone in order to suppress waste of resources. Thereafter, print data of the print job is outputted under the fixing condition set in step S65 (step S662). Further, at a time of fixing (heating) of the blank paper, the fixing condition set in step S65 is adopted as a fixing condition (particularly, a fixing speed (a heating time)). As another example, as the fixing condition of the blank paper, the fixing temperature may be set to the maximum temperature within a use range of a fixing part 133. When the maximum temperature is higher than the fixing temperature set in step S64, it is preferable to output the print data after the temperature is lowered to the set fixing temperature by preliminary rotation or cooling by a fan (not illustrated). Furthermore, the blank paper is outputted for each of sheet discharging trays 155 and 156, and the blank paper is outputted prior to the product output (output of print data) in a case of changing to a different sheet discharging tray during the print job.

Figure 17:
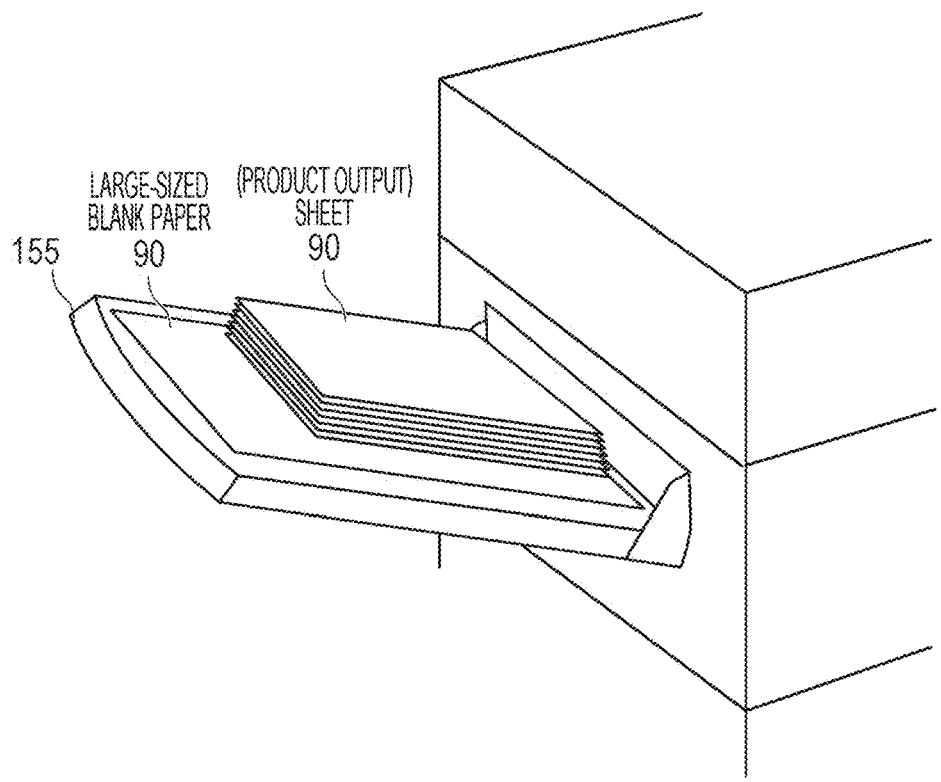
FIG. 17 is a schematic view illustrating a state in which large-sized blank paper has been discharged for care of a sheet discharging tray.

FIG. 17 is a schematic view illustrating a state in which large-sized blank paper has been discharged for care of the sheet discharging tray 155. Since there is a possibility that a virus remains in the sheet discharging tray 155 together with the sheet feeding tray 141, in the present embodiment, blank paper having a size larger than the product output is first discharged onto the sheet discharging tray 155, in order to care for the sheet discharging tray 155. Thereafter, the output of the print data (the product output) is discharged onto the same sheet discharging tray. This allows the user to collect the product output without directly touching the sheet discharging tray 155. The risk of infection can be further reduced. Further, since the blank paper is discharged to the sheet discharging tray 155 after the fixing part 133 raises the temperature of the blank paper to a higher temperature such as the maximum temperature, if a virus is attached to the sheet discharging tray 155, it is possible to kill the virus, or shorten a period until the virus is killed in natural disappearance by heating the virus with blank paper.

As described above, the image forming apparatus according to the third embodiment includes a configuration similar to that of the first embodiment. Further, when opening and closing are detected in each of the sheet feeding trays in a state where a possible carrier is "presence", the open/close history is recorded in the storage part, and the operation mode is set to the virus removal mode when the sheet feeding tray whose opening and closing have been recorded in the storage part is used in a print job. Further, when the elapsed time is equal to or longer than a predetermined period, the virus removal mode is not set. As a result, effects similar to those of the first embodiment can be obtained, and it is possible to appropriately determine whether or not the virus removal mode can be executed, so that it is possible to suppress a decrease in productivity and to reduce the risk of virus infection.

MODIFICATION

Figure 18:
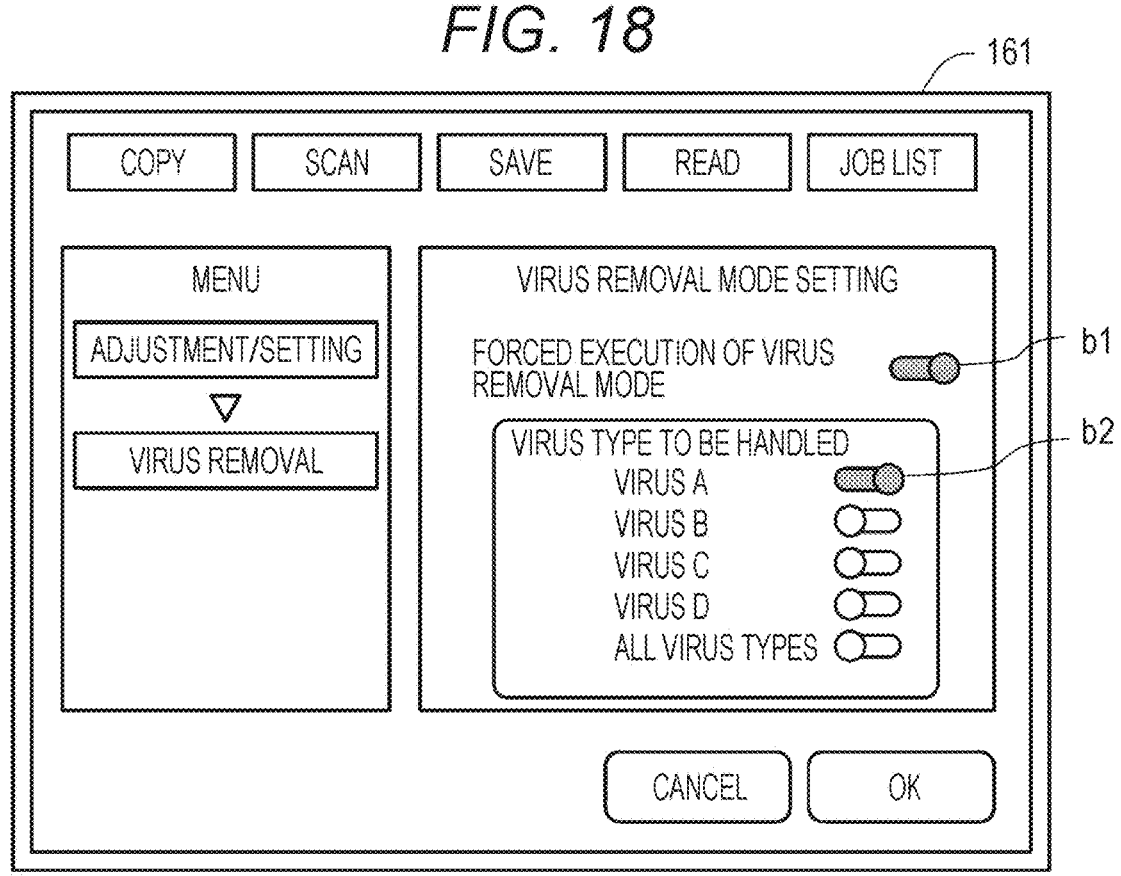
FIG. 18 is an example of a virus removal mode setting screen according to a modification.

In the first to third embodiments described above, whether or not the virus removal mode can be executed is determined on the basis of information on "presence" of a possible virus carrier in the region 80. However, as in a modification described below, a setting of forced execution of the virus removal mode by the user may be received, and the virus removal mode may be executed in response to the setting. FIG. 18 is an example of a virus removal mode setting screen 161 displayed on an operation display 16 according to the modification. In the modification, the operation display 16 functions as a reception part, and receives a setting of forced execution of the virus removal mode by the user. Note that the reception part is not limited thereto, and a hard switch may be provided in the image forming apparatus 10 to function as the reception part.

The user can enable the setting of the forced execution of the virus removal mode through a button b1 on the setting screen 161. When the setting is enabled, one or more virus types to be handled can be set through a button b2 or the like. For example, in a case where both the virus A and the virus B are set, the fixing condition is applied corresponding to the virus A having higher heat resistance. When all the viruses are selected, the fixing condition corresponding to the virus having the highest heat resistance is applied.

In the modification, when the user sets the forced execution of the virus removal mode to be enabled, the controller 11 causes a print job to be executed in the virus removal mode regardless of contents of information acquired by the acquisition part. By doing this way, in a region where an unspecified large number of users enter and leave, such as a convenience store, the image forming apparatus 10 is operated while all the users are assumed to be possible carriers. This makes it possible to further reduce the risk of virus infection.

The configuration of the image forming apparatus 10 described above has been described as a main configuration in describing the features of the above embodiments, and is not limited to the above configuration, and various modifications can be made within the scope of claims. In addition, the configuration included in a general image forming apparatus 10 is not excluded. Furthermore, the processing in the image forming apparatus 10 according to each of the above-described embodiments may include steps other than the steps illustrated in the above-described flowcharts, or may not include some of the steps described above. In addition, the order of the steps is not limited to the above-described embodiments. Furthermore, each step may be combined with another step to be executed as one step, may be included in another step to be executed, or may be divided into a plurality of steps to be executed.

OTHER MODIFICATIONS

In the example of the second embodiment (FIG. 9), an example has been described in which both of the following are performed as the fixing condition: (1) control of making the conveyance speed in the fixing part slower at the front end/rear end than that at the center of the sheet or to temporarily stop the sheet at the end part; and (2) control of executing double-sided heating in a case of thick paper even if the print setting is single-sided printing. However, one of (1) and (2) may be performed.

In addition, in the third embodiment, when the virus removal mode is performed, large-sized blank paper is discharged onto the sheet discharging tray, and then product output is performed under the set fixing condition for the virus removal mode (steps S65, S661, and S662). The process of discharging the large-sized blank paper may be exclusively performed independently. Specifically, in the example of FIG. 16, step S65 is omitted, and in steps S661 and S662, heat treatment is performed under the same fixing condition (the same fixing speed (heating time)) as the normal mode or the ecological mode. Further, as another example, the fixing temperature may be set to the maximum temperature in step S661 related to blank paper. Even in this case, it is possible to at least reduce the risk of infection via a virus attached to the sheet discharging tray.

Furthermore, in the third embodiment, an example has been described in which one remaining timer is operated for each sheet feeding tray and the operation mode is determined based on the remaining timer. However, without limiting to this, a plurality of remaining timers may be operated. For example, before the remaining timer becomes zero, all the sheets in the sheet feeding tray 141 are used (out of sheets), new sheets are replenished. At that time, if the status is "presence", the second and subsequent remaining timers are operated in parallel. Then, if any of the remaining timers is not zero, the operation mode is set to the virus removal mode. In the third embodiment described above (FIGS. 15, 16, and the like), when new replenishment is performed, the remaining timer until that time is reset if the status is "absence" at that time, but a virus may have been attached to the sheet feeding tray 141 and be transferred to the replenished sheet 90. By operating a plurality of remaining timers, the risk of virus infection due to such transfer can be reduced.

Further, means and methods to perform various kinds of processing in the image forming apparatus 10 according to the above embodiments can also be realized by either a dedicated hardware circuit or a programmed computer. The program described above may be provided by, for example, a computer-readable recording medium such as a USB memory or a digital versatile disc (DVD)-ROM, or may be provided online via a network such as the Internet. In this case, the program recorded in the computer-readable recording medium is usually transferred to and stored in a storage part such as a hard disk. In addition, the program described above may be provided as independent application software, or may be incorporated into software of the apparatus as one function of the apparatus.

Although embodiments of the present invention have been described and illustrated in detail, the disclosed embodiments are made for purposes of illustration and example only and not limitation. The scope of the present invention should be interpreted by terms of the appended claims.

What is claimed is:

1. An image forming apparatus comprising:
   one or more sheet feeding trays;
   an image forming part that includes a fixing part and forms an image on a sheet fed from each of the sheet feeding trays based on a print job; and
   an acquisition part that acquires information indicating "presence" or "absence" of a possible carrier having a possibility of virus infection in a region where an apparatus main body is installed; and
   a hardware processor that is able to select an operation mode of the print job from a normal mode and a virus removal mode, and sets an operation mode of the print job to the virus removal mode based on acquired information on the "presence", wherein in the virus removal mode, a fixing temperature of the fixing part is set to a predetermined temperature, and a heating time for the sheet in the fixing part is made longer than a heating time in the normal mode.

2. The image forming apparatus according to claim 1, wherein
when opening and closing are detected in each of the sheet feeding trays in a state of the "presence", the hardware processor records an open/close history into a storage part, and
the hardware processor sets an operation mode to the virus removal mode when executing the print job by using each of the sheet feeding trays having a record of opening and closing in the storage part.

3. The image forming apparatus according to claim 2, wherein the hardware processor does not set the virus removal mode when an elapsed time from immediately preceding opening and closing is equal to or longer than a predetermined period, even when the print job is executed using each of the sheet feeding trays having a record of opening and closing in the storage part.

4. The image forming apparatus according to claim 1, wherein
the information further includes information on a virus type, and
in the virus removal mode, the hardware processor sets a fixing temperature corresponding to the virus type.

5. The image forming apparatus according to claim 1, wherein
selectable operation modes further include an ecological mode in which a fixing temperature is set to be lower than a fixing temperature in the normal mode, and
the predetermined temperature set in the virus removal mode is higher than a fixing temperature in the ecological mode.

6. The image forming apparatus according to claim 1, wherein
the acquisition part is communicably connected to a body temperature measuring device that is provided at an entrance of the region and measures a body temperature of a person entering the region, and
the acquisition part acquires, from the body temperature measuring device, information indicating that a person whose body temperature is equal to or higher than a threshold value has entered the region, as information indicating the "presence" of a possible carrier.

7. The image forming apparatus according to claim 4, wherein
the acquisition part is communicably connected to a terminal device that is portable and carried by a user, and
as information indicating the "presence" of a possible carrier and information regarding a virus type, the acquisition part acquires
information indicating that a user who carries the terminal device is a possible carrier and information regarding a virus type, from the terminal device in the region.

8. The image forming apparatus according to claim 1, comprising:
a reception part that receives a setting operation from a user, wherein
when a setting of forced execution of the virus removal mode by a user is received from the reception part, the hardware processor executes a print job in the virus removal mode regardless of contents of the information acquired by the acquisition part.

9. The image forming apparatus according to claim 8, wherein
when information on a virus type to be handled is also received from the reception part,
in the virus removal mode, a fixing temperature corresponding to the virus type is set based on a control table describing a correspondence between the virus type and the fixing temperature.

10. The image forming apparatus according to claim 1, wherein, in the virus removal mode, when a sheet to be used is thick paper having a predetermined thickness or more or a predetermined basis weight or more, the hardware processor causes the fixing part to perform double-sided heating in which fixing is performed twice even when print setting of a print job is single-sided printing.

11. The image forming apparatus according to claim 1, wherein, in the virus removal mode, when a sheet to be used is thick paper having a predetermined thickness or more or a predetermined basis weight or more, the hardware processor makes a conveyance speed in the fixing part slower at a front end and/or a rear end of a sheet than a conveyance speed at a center of a sheet, or temporarily stops a sheet at an end part.

12. The image forming apparatus according to claim 1, wherein, in the virus removal mode, before a first output of print data of the print job, the hardware processor causes the fixing part to heat blank paper having a larger size than a sheet to be used for an output of the print data, and causes the blank paper to be discharged onto a discharging tray.

13. An image forming apparatus comprising:
a plurality of sheet feeding trays;
an image forming part that includes a fixing part and forms an image on a sheet fed from each of the sheet feeding trays based on a print job; and
an acquisition part that acquires information indicating "presence" or "absence" of a possible carrier having a possibility of virus infection in a region where an apparatus main body is installed; and
a hardware processor that is able to select at least a normal mode and a virus removal mode as an operation mode of the print job, and sets an operation mode of the print job to the virus removal mode based on acquired information on the "presence", wherein
in the virus removal mode, before a first output of print data of the print job, the fixing part is caused to heat blank paper having a larger size than a sheet to be used for an output of the print data, and the blank paper is discharged onto a discharging tray.

14. The image forming apparatus according to claim 12, wherein the hardware processor sets a fixing temperature in the fixing part to a maximum temperature within a use range, causes the blank paper to be heated, and causes the blank paper to be discharged onto the discharging tray.

15. A printing control method executed by an image forming apparatus including:
one or more sheet feeding trays, and
an image forming part that includes a fixing part and forms an image on a sheet fed from each of the sheet feeding trays based on a print job, the image forming apparatus being capable of selecting an operation mode of the print job from a normal mode and a virus removal mode, the printing control method comprising:
acquiring information indicating "presence" or "absence" of a possible carrier having a possibility of virus infection in a legion where an apparatus main body of the image forming apparatus is installed, and executing the print job in the virus removal mode based on acquired information on the "presence", wherein in the virus removal mode, a fixing temperature of the fixing part is set to a predetermined temperature, and a heating time for the sheet in the fixing part is made longer than a heating time in the normal mode.

16. The printing control method according to claim 15, comprising:

recording an open/close history in a storage part when opening and closing are detected in each of the sheet feeding trays in a state of the "presence" in the acquiring, wherein in the executing, the virus removal mode is executed when a print job is executed using each of the sheet feeding trays having a record of opening and closing in the storage part.

17. The printing control method according to claim 16, wherein, in the executing, even when the print job is executed using each of the sheet feeding trays having a record of opening and closing in the storage part, the virus removal mode is not executed when an elapsed time from immediately preceding opening and closing is equal to or longer a predetermined period.

18. A printing control method executed by an image forming apparatus including:

a plurality of sheet feeding trays; and an image forming part that includes a fixing part and forms an image on a sheet fed from each of the sheet feeding trays based on a print job, the image forming apparatus being capable of selecting an operation mode of the print job from a normal mode and a virus removal mode, the printing control method comprising:

acquiring information indicating "presence" or "absence," of a possible carrier having a possibility of virus infection in a region where an apparatus main body of the image forming apparatus is installed; and executing the print job in the virus removal mode based on acquired information on the "presence", wherein in the virus removal mode, before a first output of print data of the print job, the fixing part is caused to heat blank paper having a larger size than a sheet to be used for an output of the print data, and the blank paper is discharged onto a discharging tray.

19. The printing control method according to claim 18, wherein a fixing temperature in the fixing part is set to a maximum temperature of a use range, and the blank paper is heated and discharged onto the discharging tray.

20. A non-transitory recording medium storing a computer readable control program causing a computer to execute the printing control method according to claim 15, wherein the computer controls an image forming apparatus.

21. A non-transitory recording medium storing a computer readable control program causing a computer to execute the printing control method according to claim 18, wherein the computer controls an image forming apparatus.

* * * * *